(12) United States Patent
Levin et al.

(10) Patent No.: US 9,006,125 B2
(45) Date of Patent: *Apr. 14, 2015

(54) TRANSALKYLATION OF HEAVY AROMATIC HYDROCARBON FEEDSTOCKS

(71) Applicant: ExxonMobil Chemical Patents Inc., Baytown, TX (US)

(72) Inventors: Doron Levin, Highland Park, NJ (US); April D. Ross, Beaumont, TX (US); James H. Beech, Jr., Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/899,854

(22) Filed: May 22, 2013

(65) Prior Publication Data

US 2013/0259775 A1 Oct. 3, 2013

Related U.S. Application Data

(60) Continuation of application No. 13/449,758, filed on Apr. 18, 2012, now Pat. No. 8,481,443, which is a division of application No. 12/973,358, filed on Dec. 20, 2010, now Pat. No. 8,183,424.

(51) Int. Cl.

| | |
|---|---|
| *B01J 29/06* | (2006.01) |
| *B01J 8/04* | (2006.01) |
| *B01J 29/064* | (2006.01) |
| *B01J 29/072* | (2006.01) |
| *B01J 29/076* | (2006.01) |
| *B01J 29/44* | (2006.01) |
| *B01J 29/46* | (2006.01) |
| *B01J 29/70* | (2006.01) |
| *B01J 29/76* | (2006.01) |
| *B01J 35/00* | (2006.01) |
| *B01J 35/02* | (2006.01) |
| *B01J 37/20* | (2006.01) |
| *C07C 6/12* | (2006.01) |
| *B01J 37/00* | (2006.01) |

(52) U.S. Cl.
CPC *B01J 8/04* (2013.01); *B01J 29/064* (2013.01); *B01J 29/072* (2013.01); *B01J 29/076* (2013.01); *B01J 29/44* (2013.01); *B01J 29/46* (2013.01); *B01J 29/7034* (2013.01); *B01J 29/7669* (2013.01); *B01J 35/0006* (2013.01); *B01J 35/023* (2013.01); *B01J 37/20* (2013.01); *C07C 6/12* (2013.01); *B01J 37/0009* (2013.01); *B01J 2229/42* (2013.01); *C07C 2529/42* (2013.01)

(58) Field of Classification Search
USPC ........... 502/63, 64, 66, 67, 69, 71, 74, 77, 78, 502/79
See application file for complete search history.

(56) References Cited

U.S. PATENT DOCUMENTS

| | | | |
|---|---|---|---|
| 5,030,787 | A | 7/1991 | Absil et al. |
| 5,763,720 | A | 6/1998 | Buchanan et al. |
| 5,942,651 | A | 8/1999 | Beech, Jr. et al. |
| 6,958,425 | B1 | 10/2005 | Bogdan et al. |
| 7,419,931 | B2 | 9/2008 | Serra et al. |
| 7,544,849 | B2 | 6/2009 | Boldingh et al. |
| 7,692,052 | B2 | 4/2010 | Frey et al. |
| 2005/0202955 | A1* | 9/2005 | McMinn et al. ............... 502/64 |
| 2006/0100471 | A1 | 5/2006 | Serra Alfaro et al. |
| 2009/0112034 | A1 | 4/2009 | Levin |
| 2011/0130603 | A1* | 6/2011 | Levin ........................... 585/321 |

OTHER PUBLICATIONS

Serra et al., "A rational design of alkyl-aromatics dealkylation-transalkylation catalysts using $C_8$ and $C_9$ alkyl-aroinatics as reactants," Journal of Catalysis, 2004, vol. 227, pp. 459-469.

* cited by examiner

Primary Examiner — Elizabeth Wood

(57) ABSTRACT

In a process for producing xylene by transalkylation of a $C_9+$ aromatic hydrocarbon feedstock with a $C_6$ and/or $C_7$ aromatic hydrocarbon, the $C_9+$ aromatic hydrocarbon feedstock, at least one $C_6$ and/or $C_7$ aromatic hydrocarbon and hydrogen are contacted with a first catalyst comprising (i) a first molecular sieve having a Constraint Index in the range of about 3 to about 12 and (ii) at least first and second different metals or compounds thereof of Groups 6 to 12 of the Periodic Table of the Elements. Contacting with the first catalyst is conducted under conditions effective to dealkylate aromatic hydrocarbons in the feedstock containing $C_2+$ alkyl groups and to saturate $C_2+$ olefins formed so as to produce a first effluent. At least a portion of the first effluent is then contacted with a second catalyst comprising a second molecular sieve having a Constraint Index less than 3 under conditions effective to transalkylate $C_9+$ aromatic hydrocarbons with said at least one $C_6$-$C_7$ aromatic hydrocarbon to form a second effluent comprising xylene.

8 Claims, 1 Drawing Sheet

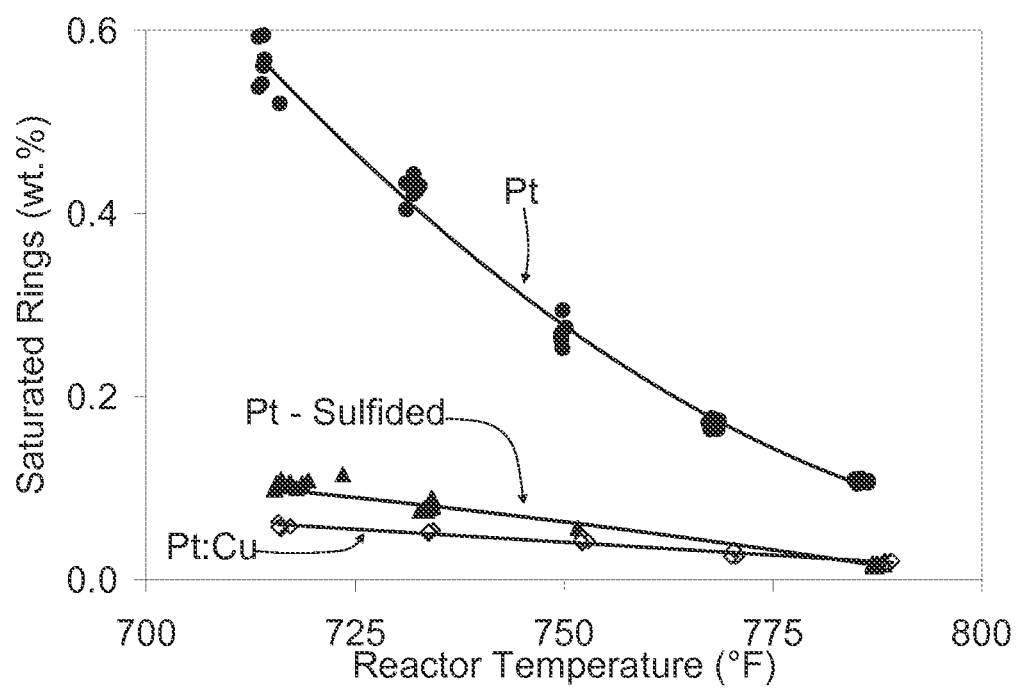

TRANSALKYLATION OF HEAVY AROMATIC HYDROCARBON FEEDSTOCKS

CROSS REFERENCE TO RELATED APPLICATIONS

This application is a Continuation of U.S. application Ser. No. 13/449,758, filed Apr. 18, 2012, now U.S. Pat. No. 8,481,443, which is a Divisional of U.S. Pat. No. 8,183,424, filed Dec. 20, 2010, all of which claim the benefit of and priority to U.S. Provisional Application Ser. No. 61/301,055, filed Feb. 3, 2010, and the disclosures of which are fully incorporated herein by reference.

FIELD

This invention relates to transalkylation of heavy ($C_9$+) aromatic hydrocarbon feedstocks to produce xylene.

BACKGROUND

An important source of xylene in an oil refinery is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains benzene, toluene and xylenes (BTX), along with ethylbenzene.

However, the quantity of xylene available from reforming is limited and so recently refineries have also focused on the production of xylene by transalkylation of $C_9$+ aromatic hydrocarbons with benzene and/or toluene over noble metal-containing zeolite catalysts. One such process, using MCM-22 as the zeolite catalyst is disclosed in U.S. Pat. No. 5,030,787. However, during the transalkylation of $C_9$+ aromatics with, for example, toluene to produce xylem and benzene, saturated by-products, which boil in the same temperature range as the desired aromatic products, are typically produced making separation of the desired products at high purity levels difficult. For example, a commercial benzene product may need a purity of 99.85 wt % or higher. However, initial benzene purity after distillation of a transalkylation reaction product is typically only 99.2% to 99.5% due to the presence of coboilers, such as methylcyclopentane, cyclohexane, 2,3-dimethylpentane, dimethylcyclopentane and 3-methylhexane. Therefore, an additional extraction step is usually required to further improve benzene product purity to the desired level.

One solution to the problem of the production of benzene co-boilers during the transalkylation of heavy aromatics is disclosed in U.S. Pat. No. 5,942,651 and involves the steps of contacting a feed comprising $C_9$+ aromatic hydrocarbons and toluene under transalkylation reaction conditions with a first catalyst composition comprising a zeolite having a constraint index ranging from 0.5 to 3, such as ZSM-12, and a hydrogenation component. The effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product composition comprising benzene and xylene. A benzene product having a purity of at least 99.85% may be obtained by distilling the benzene from the transalkylation reaction product, without the need for an additional extraction step. According to the '651 patent, the second catalyst composition comprises up to 20 wt % of the total weight of the first and second catalyst compositions.

Another problem associated with heavy aromatics alkylation processes is catalyst aging since, as the catalyst cokes with increasing time on stream, higher temperatures are normally required to maintain constant conversion. When the maximum reactor temperature is reached, the catalyst needs to be replaced or regenerated. Depending on the $C_9$+:$C_6$ or $C_7$ composition of the feed, the cycle length may vary from only 9 months for high $C_9$+:$C_7$ ratios of 85:15 to about 5 years for low $C_9$+:$C_7$ ratios of 20:80. Recent work has shown that the aging rate of existing transalkylation catalysts is also strongly dependent on the presence in the feed of aromatic compounds having alkyl substitutents with two or more carbon atoms, such as ethyl and propyl groups. Thus these compounds tend to undergo disproportionation to produce $C_{10}$+ coke precursors.

To address the problem of $C_9$+ feeds containing high levels of ethyl and propyl substituents, U.S. Published Application No. 2009/0112034 discloses a catalyst system adapted for transalkylation a $C_9$+ aromatic feedstock with a $C_6$-$C_7$ aromatic feedstock comprising: (a) a first catalyst comprising a first molecular sieve having a Constraint Index in the range of 3-12 and 0.01 to 5 wt % of at least one source of a first metal element of Groups 6-10; and (b) a second catalyst comprising a second molecular sieve having a Constraint Index less than 3 and 0 to 5 wt % of at least one source of a second metal element of Groups 6-10, wherein the weight ratio of said first catalyst to said second catalyst is in the range of 5:95 to 75:25. The first catalyst, which is optimized for dealkylation of the ethyl and propyl groups in the feed, is located in front of said second catalyst, which is optimized for transalkylation, when they are brought into contact with said $C_9$+ aromatic feedstock and said $C_6$-$C_7$ aromatic feedstock in the presence of hydrogen.

Whereas the multiple catalyst bed system of U.S. Published Application No. 2009/0112034 represents a significant improvement over single catalyst bed processes for the transalkylation of heavy aromatic feeds, it suffers from the disadvantage that the first catalyst, in addition to dealkylating ethyl and propyl substituted aromatics and saturating the resultant olefins, tends to facilitate the side reaction of aromatics saturation. This reaction is primarily a concern at the start of cycle when the reactor temperature is at its lowest and is undesirable since it reduces aromatic yield and generates saturated products. In addition, some of these saturated products, e.g. cyclohexane and methylcyclohexane, have boiling points close to benzene which makes it difficult to recover high purity benzene. Although this problem can be alleviated by sulfiding the metal catalysts on start-up to reduce their aromatic saturation activity, this is often undesirable as it necessitates adding the facilities and sulfiding agents to effect the metal sulfidation.

The present invention seeks to provide a $C_9$+ aromatic transalkylation process that retains the advantages of the multiple bed catalyst system while reducing the problem of aromatic saturation without the need for pre-sulfidation of the catalysts.

SUMMARY

In one aspect, the invention resides in a process for producing xylene by transalkylation of a $C_9$+ aromatic hydrocarbon feedstock with a $C_6$ and/or $C_7$ aromatic hydrocarbon, the process comprising:

(a) contacting a $C_9+$ aromatic hydrocarbon feedstock, at least one $C_6$ and/or $C_7$ aromatic hydrocarbon and hydrogen with a first catalyst under conditions effective to dealkylate aromatic hydrocarbons in the feedstock containing $C_2+$ alkyl groups and to saturate $C_2+$ olefins formed so as to produce a first effluent, the first catalyst comprising (i) first molecular sieve having a Constraint Index in the range of about 3 to about 12 and (ii) at least first and second different metals or compounds thereof of Groups 6 to 12 of the Periodic Table of the Elements; and then (b) contacting at least a portion of said first effluent with a second catalyst comprising a second molecular sieve having a Constraint Index less than 3 under conditions effective to transalkylate $C_9+$ aromatic hydrocarbons with said at least one $C_6$-$C_7$ aromatic hydrocarbon to form a second effluent comprising xylem.

Conveniently, first metal is at least one of platinum, palladium, iridium, and rhenium and the second metal is at least one of copper, silver, gold, ruthenium, iron, tungsten, molybdenum, cobalt, nickel, tin and zinc.

In one embodiment, the first metal comprises platinum and said second metal comprises copper.

Conveniently, the first metal is present in the first catalyst in amount between about 0.001 and about 5 wt % of the first catalyst and the second metal is present in the first catalyst in amount between about 0.001 and about 10 wt % of the first catalyst.

Conveniently, said first molecular sieve comprises at least one of ZSM-5, ZSM-11, ZSM-22, ZSM-23, ZSM-35, ZSM-48, ZSM-57 and ZSM-58. Conveniently, the second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22 MCM-36 MCM-49 MCM-56, EMM-10, EMM-10-P and ZSM-20. In one embodiment, the said first molecular sieve is ZSM-5 and the second molecular sieve is ZSM-12.

Conveniently, the first molecular sieve has an alpha value in the range of 100 to 1500 and the second molecular sieve has an alpha value in the range of 20 to 500.

Conveniently, the second catalyst also comprises the same first and second metals or compounds thereof as the first catalyst.

Conveniently, the weight ratio of the first catalyst to the second catalyst is in the range of 5:95 to 75:25.

Conveniently, the conditions employed in the contacting (a) and (b) comprise a temperature in the range of about 100 to about 800° C., a pressure in the range of about 790 to about 7000 kPa-a, a $H_2$:HC molar ratio in the range of about 0.01 to about 20, and a WHSV in the range of about 0.01 to about 100 $hr^{-1}$.

Conveniently, the process further comprises (c) contacting at least a portion of said second effluent comprising xylene with a third catalyst comprising a third molecular sieve having a Constraint Index in the range of about 3 to about 12 under conditions effective to crack non-aromatic cyclic hydrocarbons in said second effluent and form a third effluent comprising xylem; and (d) recovering xylene from said third effluent.

In a further aspect, the invention resides in a catalyst system adapted for transalkylation a $C_9+$ aromatic hydrocarbon feedstock with a $C_6$-$C_7$ aromatic hydrocarbon, the catalyst system comprising:

(a) a first catalyst bed comprising (i) a first molecular sieve having a Constraint Index in the range of about 3 to about 12 and (ii) at least first and second different metals or compounds thereof of Groups 6 to 12 of the Periodic Table of the Elements having different benzene saturation activity; and (b) a second catalyst bed comprising a second molecular sieve having a Constraint Index less than 3;

wherein the weight ratio of said first catalyst to said second catalyst is in the range of about 5:95 to about 75:25 and wherein said first catalyst bed is located upstream of said second catalyst bed when the catalyst system is brought into contact with said $C_9+$ aromatic hydrocarbon feedstock and said $C_6$-$C_7$ aromatic hydrocarbon in the presence of hydrogen.

BRIEF DESCRIPTION OF THE DRAWINGS

FIG. 1 is a graph plotting wt % saturated aromatic rings against reactor temperature for the $C_9+$ aromatic transalkylation process of Example 1 employing a Pt/ZSM-5 catalyst, a sulfided Pt/ZSM-5 catalyst and a PtCu/ZSM-5 catalyst.

DETAILED DESCRIPTION

Described herein are a process and a multi-bed catalyst system for producing xylene by transalkylation of a heavy aromatic hydrocarbon feedstock with a $C_6$ and/or $C_7$ aromatic hydrocarbon. In particular, the catalyst system comprises at least two, and optionally three, catalyst beds which are arranged so that a first catalyst bed is located upstream of the second catalyst bed and, if present, the third catalyst bed is located downstream of the second catalyst bed, when the catalyst system is brought into contact with the heavy aromatic hydrocarbon feedstock and the $C_6$-$C_7$ aromatic hydrocarbon. The first catalyst bed is effective to dealkylate aromatic hydrocarbons in the heavy aromatic feedstock containing $C_2+$ alkyl groups and to saturate the resulting $C_2+$ olefins, whereas the second catalyst bed is effective to transalkylate the heavy aromatic hydrocarbons with the $C_6$-$C_7$ aromatic hydrocarbon to produce xylenes. The optional third catalyst bed is effective to crack non-aromatic cyclic hydrocarbons in effluent from the first and second catalyst beds.

Feedstocks

As used herein the term "$C_n+$", wherein n is a positive integer, means a compound or group containing at least n carbon atoms. In addition, the term "$C_n+$ aromatic hydrocarbon feedstock", wherein n is a positive integer, means that a feedstock comprising greater than 50 wt % of aromatic hydrocarbons having at least n number of carbon atom(s) per molecule.

Thus the heavy aromatic feedstock used in the present process comprises greater than 50 wt %, conveniently at least 80 wt %, typically at least 90 wt %, of one or more aromatic compounds containing at least 9 carbon atoms. Specific $C_9+$ aromatic compounds found in a typical feed include mesitylene (1,3,5-trimethylbenzene), durene (1,2,3,4,5-tetramethylbenzene), hemimellitene (1,2,4-trimethylbenzene), pseudocumene (1,2,4-trimethylbenzene), ethyltoluenes, ethylxylenes, propyl-substituted benzenes, butyl-substituted benzenes, and dimethylethylbenzenes. Suitable sources of the $C_9+$ aromatics are any $C_9+$ fraction from any refinery process that is rich in aromatics, such as catalytic reformate, FCC naphtha or TCC naphtha.

The feed to the process also includes benzene and/or toluene, typically toluene. The feed may also include unreacted toluene and $C_9+$ aromatic feedstock that is recycled after separation of the xylene product from the effluent of the transalkylation reaction. Typically, the $C_6$ and/or $C_7$ aromatic hydrocarbon constitutes up to 90 wt %, such as from 10 to 70 wt % of the entire feed, whereas the $C_9+$ aromatics component constitutes at least 10 wt %, such as from 30 to 85 wt %, of the entire feed to the transalkylation reaction.

The feedstock may be characterized by the molar ratio of methyl groups to single aromatic rings. In some embodiments, the combined feedstock (the combination of the $C_9+$ and the $C_1$-$C_7$ aromatic feedstocks) has a molar ratio of methyl groups to single aromatic rings in the range of from 0.5 to 4, such as from 1 to 2.5, for example from 1.5 to 2.25.

First Catalyst Bed

The first catalyst bed employed in the present catalyst system accommodates a first catalyst comprising a first molecular sieve having a Constraint Index in the range of about 3 to about 12 and at least first and second different metals or compounds thereof of Groups 6 to 12 of the Periodic Table of the Elements.

Constraint Index is a convenient measure of the extent to which an aluminosilicate or other molecular sieve provides controlled access to molecules of varying sizes to its internal structure. For example, molecular sieves which provide a highly restricted access to and egress from its internal structure have a high value for the Constraint Index. Molecular sieves of this kind usually have pores of small diameter, e.g. less than 5 Angstroms. On the other hand, molecular sieves which provide relatively free access to their internal pore structure have a low value for the Constraint Index, and usually pores of large size. The method by which constraint index is determined is described fully in U.S. Pat. No. 4,016,218, which is incorporated herein by reference for the details of the method.

Suitable molecular sieves for use in the first catalyst comprise at least one of ZSM-5, ZSM-11, ZSM-22, ZSM-23, ZSM-35, ZSM-48, ZSM-57 and ZSM-58. ZSM-5 is described in detail in U.S. Pat. No. 3,702,886 and Re. Pat. No. 29,948, ZSM-11 is described in detail in U.S. Pat. No. 3,709,979. ZSM-22 is described in U.S. Pat. Nos. 4,556,477 and 5,336,478. ZSM-23 is described in U.S. Pat. No. 4,076,842. ZSM-35 is described in U.S. Pat. No. 4,016,245. ZSM-48 is more particularly described in U.S. Pat. Nos. 4,234,231 and 4,375,573, ZSM-57 is described in U.S. Pat. No. 4,873,067. ZSM-58 is described in U.S. Pat. No. 4,698,217.

In one preferred embodiment, the first molecular sieve comprises ZSM-5 and especially ZSM-5 having an average crystal size of less than 0.1 micron, such as about 0.05 micron.

Conveniently, the first molecular sieve has an alpha value in the range of about 100 to about 1500, such as about 150 to about 1000, for example about 300 to about 600. Alpha value is a measure of the cracking activity of a catalyst and is described in U.S. Pat. No. 3,354,078 and in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, page 395.

Generally, the first molecular sieve is an aluminosilicate having a silica to alumina molar ratio of less than 1000, typically from about 10 to about 100.

Typically, the first catalyst comprises at least 1 wt %, preferably at least 10 wt %, more preferably at least 50 wt %, and most preferably at least 65 wt %, of the first molecular sieve.

In addition to a molecular sieve having a Constraint Index in the range of about 3 to about 12, the first catalyst comprises at least first and second different metals or compounds thereof of Groups 6 to 12 of the Periodic Table of the Elements. As used herein, the numbering scheme for the Periodic Table Groups is used as in Chemical and Engineering News, 63(5), 27 (1985).

The first metal is generally selected from platinum, palladium, iridium, rhenium and mixtures thereof, whereas the second metal is chosen so as to lower the benzene saturation activity of the first metal and is conveniently selected from at least one of copper, silver, gold, ruthenium, iron, tungsten, molybdenum, cobalt, nickel, tin and zinc. In one embodiment, the first metal comprises platinum and said second metal comprises copper.

Conveniently, the first metal is present in the first catalyst in an amount between about 0.001 and about 5 wt % of the first catalyst and the second metal is present in the first catalyst in amount between about 0.001 and about 10 wt % of the first catalyst.

In most cases, the first catalyst also comprises a binder or matrix material that is resistant to the temperatures and other conditions employed in the present transalkylation process. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides. Use of a binder or matrix material which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may include, for example, naturally occurring clays, e.g. bentonite and kaolin, to improve the crush strength of the catalyst composition under commercial operating conditions.

Naturally occurring clays that can be composited with the first molecular sieve as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the first molecular sieve can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form so as to facilitate extrusion of the catalyst composition.

Typically the first molecular sieve is admixed with the binder or matrix material so that the first catalyst composition contains the binder or matrix material in an amount ranging from 5 to 95 wt %, and typically from 10 to 60 wt %.

Second Catalyst Bed

The second catalyst bed accommodates a second catalyst comprising a second molecular sieve having a Constraint Index less than 3 and optionally one or more metals or compounds thereof of Groups 6 to 12 of the Periodic Table of the Elements.

Suitable molecular sieves for use in the second catalyst composition comprise at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, PSH-3, SSZ-25, MCM-36, MCM-49, MCM-56, EMM-10, EMM-10-P and ZSM-20. Zeolite ZSM-4 is described in U.S. Pat. No. 3,923,636. Zeolite ZSM-12 is described in U.S. Pat. No. 3,832,449. Zeolite ZSM-20 is described in U.S. Pat. No. 3,972,983. Zeolite Beta is described in U.S. Pat. No. 3,308,069, and Re. Pat. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277. MCM-49 is described in U.S. Pat. No. 5,236,575. MCM-56 is described in U.S. Pat. No. 5,362,697.

In one preferred embodiment, the second molecular sieve comprises ZSM-12 and especially ZSM-12 having an average crystal size of less than 0.1 micron, such as about 0.05 micron.

Conveniently, the second molecular sieve has an alpha value of at least 20, such as from about 20 to about 500, for example from about 30 to about 100.

Generally, the second molecular sieve is an aluminosilicate having a silica to alumina molar ratio of less than 500, typically from about 50 to about 300.

Typically, the second catalyst comprises at least 1 wt %, preferably at least 10 wt %, more preferably at least 50 wt %, and most preferably at least 65 wt %, of the second molecular sieve.

Optionally, the second catalyst comprises at least one and preferably at least two metals or compounds thereof of Groups 6 to 12 of the Periodic Table of the Elements. Generally, the second catalyst comprises the same first and second metals present in the same amounts as contained by the first catalyst.

Generally, the second catalyst also contains a binder or matrix material, which can be any of the materials listed as being suitable for the first catalyst and can be present in an amount ranging from 5 to 95 wt %, and typically from 10 to 60 wt %, of the second catalyst composition.

Conveniently, the weight ratio of the first catalyst to the second catalyst is in the range of 5:95 to 75:25.

Optional Third Catalyst Bed

In addition to the first and second catalysts beds employed in the present multi-bed catalysts system, it may be desirable to incorporate a third catalyst bed downstream of the second catalyst bed and effective to crack non-aromatic cyclic hydrocarbons in the effluent from the first and second catalyst beds. The third catalyst bed accommodates a third catalyst comprising a third molecular sieve having a Constraint Index from about 1 to 12. Suitable molecular sieves for use in the third catalyst comprise at least one of ZSM-5, ZSM-11, ZSM-12, zeolite beta, ZSM-22, ZSM-23, ZSM-35, ZSM-48, ZSM-57 and ZSM-58, with ZSM-5 being preferred.

Production of the Catalysts

The metal components of the first and second catalysts can be incorporated into the catalyst composition by co-crystallization, exchanged into the composition to the extent a Group 13 element, e.g., aluminum, is in the molecular sieve structure, impregnated therein, or mixed with the molecular sieve and binder. For example, the metal components can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum ammine complex, such as $Pt(NH_3)_4Cl_2H_2O$. Alternatively, a compound of the hydrogenation component may be added to the molecular sieve when it is being composited with a binder, or after the molecular sieve and binder have been formed into particles by extrusion or pelletizing. The second metal component may be incorporated into the catalyst composition at the same time and in the same manner as the first metal component. Alternatively, the second metal component may be incorporated into the catalyst composition after the first metal component has been incorporated, and this may be achieved in the same or an alternative manner.

After incorporation of the metal components, the molecular sieve is usually dried by heating at a temperature of 65° C. to 160° C., typically 110° C. to 143° C., for at least 1 minute and generally not longer than 24 hours, at pressures ranging from 100 to 200 kPa-a. Thereafter, the molecular sieve may be calcined in a stream of dry gas, such as air or nitrogen, at temperatures of from 260° C. to 650° C. for 1 to 20 hours. Calcination is typically conducted at pressures ranging from 100 to 300 kPa-a.

Although one advantage of the present multi-bed catalyst system is that its aromatic hydrogenation activity is low, in some cases it may be desirable to steam treat and/or sulfide one of more of the catalyst beds prior to use. Steam treatment may be effected by contacting the catalyst composition with from 5 to 100% steam at a temperature of at least 260 to 650° C. for at least one hour, typically from 1 to 20 hours, at a pressure of 100 to 2590 kPa-a. Sulfiding is conveniently accomplished by contacting the catalyst with a source of sulfur, such as hydrogen sulfide, at a temperature ranging from about 320 to 480° C. for a period of about 1 to about 24 hours.

Transalkylation Apparatus and Process

The first and second catalyst beds and, if present, the third catalyst bed may be located in separate reactors but are conveniently located in a single reactor, typically separated from another by spacers or by inert materials, such as, alumina balls or sand. Alternatively, the first and second catalyst beds could be located in one reactor and the third catalyst bed located in a different reactor. As a further alternative, the first catalyst bed could be located in one reactor and the second and third catalyst beds located in a different reactor. In all situations, the first catalyst is not mixed with the second catalyst and the hydrocarbon feedstocks and hydrogen are arranged to contact the first catalyst bed prior to contacting the second catalyst bed. Similarly, if the third catalyst bed is present, the hydrocarbon feedstocks and hydrogen are arranged to contact the second catalyst bed prior to contacting the third catalyst bed.

In operation, the first catalyst bed is maintained under conditions effective to dealkylate aromatic hydrocarbons containing $C_2+$ alkyl groups in the heavy aromatic feedstock and to saturate the resulting $C_2+$ olefins. Suitable conditions for operation of the first catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 hr preferably about 2 to about 20 $hr^{-1}$.

The second catalyst bed is maintained under conditions effective to transalkylate $C_9+$ aromatic hydrocarbons with said at least one $C_6$-$C_7$ aromatic hydrocarbon. Suitable conditions for operation of the second catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 hr$^{-1}$, preferably about 1 to about 10 hr$^{-1}$.

Where present, the third catalyst bed is maintained under conditions effective to crack non-aromatic cyclic hydrocarbons in the effluent from the second catalyst bed. Suitable conditions for operation of the third catalyst bed comprise a temperature in the range of about 100 to about 800° C., preferably about 300 to about 500° C., a pressure in the range of about 790 to about 7000 kPa-a, preferably about 2170 to 3000 kPa-a, a $H_2$:HC molar ratio in the range of about 0.01 to about 20, preferably about 1 to about 10, and a WHSV in the range of about 0.01 to about 100 hr$^{-1}$, preferably about 1 to about 50 hr$^{-1}$.

Obviously, where the first, second and optional third catalyst beds are located in a single reactor, the operating conditions in each bed are substantially the same.

The invention will now be more particularly described with reference to the Examples and accompanying drawing.

Examples 1 to 3

Dealkylation of Heavy Aromatics Feed Using Bi-Metallic MFI Zeolite

A ZSM-5 zeolite having a Si/Al$_2$ molar ratio of 65 and crystal dimensions of 0.14 μm was formulated into a 1/16" cylindrical extrudate (Examples 1 and 3) or 1/20" quadrilobe extrudate (Example 2) using a Versal 300 alumina binder such that the mass ratio of zeolite crystal to alumina was 1:1, A Cu or CuPt solution was added during mulling to create 0.115 wt % Pt catalyst (Examples 1 and 3) or 0.115 wt % Pt, 0.0375 wt % Cu catalyst (Example 2). The extrudates were converted into the acidic form by calcining at 538° C. for 2 hours and then steamed at 800° F. (427° C.) for 3 hours in 100% steam to moderate their catalytic activity. The resultant catalysts were then tested in a fixed-bed microunit. The reactor pressure was 350 psig (2514 kPa) and the $H_2$:HC ratio was 2:1. The feed to the reactor contained 85% heavy aromatics and 15% benzene+toluene, A detailed analysis of the feed is shown in Table 1.

TABLE 1

| Feed Composition | % |
| --- | --- |
| C5-gas | 0.00 |
| Benzene | 8.55 |
| Toluene | 6.39 |
| Ethylbenzene | 0.00 |
| Xylenes | 0.21 |
| EthylToluene | 22.93 |
| Trimethylbenzene | 39.09 |
| Proplybenzene | 2.65 |
| 1,n-ethylxylene | 10.56 |
| Tetramethylbenzene | 2.45 |
| Other C10 aromatic | 5.31 |
| Other C11 aromatic | 0.30 |
| Other C12 aromatic | 0.00 |
| Indanes | 0.74 |
| Alkylindanes | 0.00 |

TABLE 1-continued

| Feed Composition | % |
| --- | --- |
| Napthalene | 0.01 |
| Alkylnaphthalene | 0.00 |
| Heavies | 0.00 |
| Unidentified | 0.80 |

The catalysts were reduced in hydrogen for 1 hour at 410-420° C. prior to the introduction of feed. The catalysts of Examples 1 and 2 were tested with just the hydrogen reduction prior to feed introduction, whereas the catalyst of Example 3 was subjected to $H_2S$ sulfiding after hydrogen reduction using 400 ppm $H_2S$ in hydrogen at 420° C. The total amount of sulfur added to the reactor was 5 moles S per mole Pt prior to feed introduction, and a further 10 moles S per mole Pt after the feed was introduced. The activity of the catalysts was determined at 350 psig (2514 kPa) with a $H_2$:HC molar ratio of 2:1. The total feed flowrate, expressed as grams feed per gram catalyst per hour (WHSV) was 10 hr$^{-1}$. Product analysis occurred using on-line GC-FUD with a 60 m DB-WAX column. The results are summarized in Table 2 and FIG. 1.

TABLE 2

| | Example | | |
| --- | --- | --- | --- |
| | 1 | 2 | 3 |
| Catalyst Metal | 0.115% Pt | 0.115% Pt 0.0375% Cu | 0.115% Pt |
| WHSV | 10 | 10 | 13.3 |
| Pre-/Co-sulfiding | 0/0 | 0/0 | 5/10 |
| Average Reactor Temperature, ° F. | 786 | 789 | 788 |
| Total xylenes | 14.6 | 16.2 | 13.6 |
| Ethylbenzene | 0.3 | 0.7 | 1.1 |
| PX/Total xylenes, % | 24.3 | 24.2 | 24.3 |
| PX purity, % | 23.8 | 23.2 | 22.5 |
| Ethyltoluene conversion, % | 97.0 | 95.0 | 90.5 |
| Ethylxylene conversion, % | 73.6 | 72.4 | 58.4 |
| 1,3,5-TMB conversion, % | −1.8 | 2.3 | −2.0 |
| 1,2,4-TMB conversion, % | 21.9 | 26.6 | 22.0 |
| 1,2,3-TMB conversion, % | 29.9 | 32.2 | 23.6 |
| C9 conversion, % | 45.9 | 48.0 | 43.4 |
| C10 conversion, % | 59.3 | 56.5 | 48.0 |
| C9/10 conversion, % | 48.7 | 49.8 | 44.3 |
| Toluene + C9/10 conversion, % | 28.3 | 29.2 | 25.5 |
| Total TMBs | 34.13 | 32.35 | 34.43 |
| Total TeMBs | 4.43 | 4.78 | 4.87 |
| Total 218° C.+ BP | 0.84 | 1.41 | 1.52 |
| % Deethylation | 89.7 | 88.0 | 80.4 |
| % Depropylation | 99.4 | 99.0 | 98.3 |
| Total saturates | 0.11 | 0.02 | 0.02 |
| Benzene purity, % | 98.89 | 99.81 | 99.83 |
| Light gas | 10.5 | 8.2 | 7.3 |

Comparison of the feed and product compositions in Tables 1 and 2 respectively shows that the all catalysts were very effective for dealkylating the feed without catalyzing transalkylation reactions to any significant extent. The Pt-non-sulfided (Example 1) and Pt—Cu system (Example 2) had very similar de-ethylation rates between 88-90%. The Pt-sulfided system (Example 3) was slightly lower at 80%. However, the saturates produced with the Pt-non-sulfided system (Example 1) were much higher at 0.11 wt % than those produced with the Pt—Cu and Pt-sulfided systems, which had 0.02 wt % saturates. This point is further illustrated in FIG. 1, showing the saturated rings as a function of temperature for the 3 catalyst systems. As expected, the Pt-non-sulfided catalyst (Example 1) saturated increasing more rings as the temperature decreased. Both the bimetallic catalyst (Example 2) and the sulfided Pt-only catalyst (Example 3) showed significantly reduced ring saturation at lower temperatures.

Example 4

Dual Bed Heavy Aromatics Transalkylation

The transalkylation of heavy aromatics with benzene and toluene was demonstrated over a dual bed catalyst system in a fixed-bed microunit. The following catalyst systems were evaluated:

System A
    Top Bed: 0.115 wt % Pt, 50:50 ZSM-5B:Al2O3
    Mid Bed: 0.1 wt % Pt/65:35 ZSM-12:Al2O3

System B
    Top Bed: 0.115 wt % Pt/0.0375 wt % Cu/50:50 ZSM-5B:Al2O
    Mid Bed: 0.1 wt % Pt/0.0326 wt % Cu/65:35 ZSM-12:Al2O3

The reactor pressure was 350 psig (2514 kPa), the WHSV was 4 and the $H_2$:HC ratio was 2:1. The feed to the reactor contained 60% heavy aromatics and 40% toluene. A detailed analysis of the feed is shown in Table 3. On start-up, the catalyst beds were reduced in hydrogen at 420° C. The platinum only catalyst system (A) was subjected to $H_2S$ sulfiding after hydrogen reduction. The total amount of sulfur added to the reactor was 7 moles S per mole Pt prior to feed introduction, and a further 10 moles S per mole Pt after feed was introduced. Product analysis was conducted using on-line GC-FID. The results are summarized in Table 4.

TABLE 3

| | |
|---|---|
| C5-gas | 0.0 |
| Benzene | 0.0 |
| Toluene | 41.4 |
| Ethylbenzene | 0.0 |
| Xylenes | 0.1 |
| Ethyltoluene | 14.0 |
| Trimethylbenzene | 29.2 |
| Proplybenzene | 1.9 |
| 1,n-ethyl xylene | 6.2 |
| Tetramethylbenzene | 2.8 |
| Other C10 aromatics | 2.9 |
| Other C11 aromatics | 0.4 |
| Other C12 aromatics | 0.0 |
| Indanes | 0.5 |
| Alkylindanes | 0.2 |
| Napthalene | 0.1 |
| Alkynapthalene | 0.0 |
| Heavies | 0.0 |
| Unidentified | 0.2 |

TABLE 4

| | Catalyst system | |
|---|---|---|
| | A | B |
| Pre-/Co-sulfiding | 7/10 | 0/0 |
| Days on stream | 16.4 | 6.3 |
| Average reactor temperature ° F. | 767 | 765 |
| Catalyst Performance | | |
| % Deethylation | 70.7 | 80.6 |
| % Depropylation | 95.9 | 96.7 |
| C2/C2 = | 1161 | 2521 |
| C3/C3 = | 875 | |
| Benzene purity, % | 99.26 | 99.10 |
| Conversion % | | |
| Toluene | 31.2 | 32.3 |
| C9 | 58.1 | 60.2 |
| C10 | 60.5 | 67.3 |
| Toluene + C9 + C10 | 47.6 | 49.4 |
| Ring loss (Naph. = 1 ring), % | 2.6 | 3.1 |

TABLE 4-continued

| | Catalyst system | |
|---|---|---|
| | A | B |
| Yields, wt % | | |
| Light gas (C5-) | 7.8 | 8.7 |
| Non-aromatics | 0.3 | 0.2 |
| Benzene | 6.1 | 6.5 |
| Toluene | 27.5 | 28.0 |
| Ethylbenzene | 1.2 | 0.8 |
| Xylenes | 31.9 | 33.5 |
| C9 aromatics | 19.6 | 18.2 |
| MeBenzenes | 2.9 | 1.9 |
| TMB | 16.5 | 16.2 |
| C10 aromatics | 4.9 | 4.0 |
| Diethylbenzenes | 0.06 | 0.02 |
| Dimethylethylbenzenes | 1.9 | 1.3 |
| Tetramethylbenzene | 2.6 | 2.5 |
| C11+ aromatics | 1.3 | 0.9 |
| Naphthalenes | 0.5 | 0.6 |

As the data in Table 3 indicates, system B has higher de-ethylation/de-propylation rates and slightly higher conversion with only slightly higher ring loss (2.6 vs 3.1). If brought to the same de-ethylation and conversion, the ring loss for the two systems would be very similar, illustrating the suitable use of bi-metallic catalyst system to replace a platinum only system when sulfiding is not preferred. The higher ethane to ethylene ratio for the bimetallic system indicates good metal function for ethylene saturation, which is desired.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:
1. A catalyst system comprising:
(a) a first catalyst bed comprising (i) a first molecular sieve having a Constraint Index in the range of about 3 to about 12 and (ii) at least one metal selected from platinum, palladium, iridium, and rhenium, in an amount between about 0.001 and about 5 wt % of the first catalyst, and at least one metal selected from copper, silver, gold, ruthenium, iron, tungsten, molybdenum, cobalt, nickel, tin and zinc, in an amount between about 0.001 and about 10 wt % of the first catalyst; and
(b) a second catalyst bed comprising (i) a second molecular sieve having a Constraint Index less than 3 and (ii) at least one metal selected from platinum, palladium, iridium, and rhenium, in an amount between about 0.001 and about 5 wt % of the second catalyst, and at least one metal selected from copper, silver, gold, ruthenium, iron, tungsten, molybdenum, cobalt, nickel, tin and zinc, in an amount between about 0.001 and about 10 wt % of the second catalyst;
wherein the weight ratio of said first catalyst to said second catalyst is in the range of about 5:95 to about 75:25 and wherein said first catalyst bed is located upstream of said second catalyst bed when the catalyst system is brought into contact with said C9+ aromatic hydrocarbon feedstock and said C6-C7 aromatic hydrocarbon in the presence of hydrogen;
(c) a third catalyst bed comprising a third molecular sieve having a Constraint Index in the range of about 3 to about 12, said catalyst system further characterized as comprising, in series, said first catalyst bed, then said second catalyst bed, then said third catalyst bed.

2. The catalyst system of claim 1, wherein said first catalyst bed comprises platinum and copper.

3. The catalyst system of claim 1, wherein said second catalyst bed comprises platinum and copper.

4. The catalyst system of claim 1, wherein said first catalyst bed comprises platinum and copper, and said second catalyst bed comprises platinum and copper.

5. The catalyst system of claim 1, wherein said first molecular sieve comprises at least one of ZSM-5, ZSM-11, ZSM-22, ZSM-23, ZSM-35, ZSM-48, ZSM-57, and ZSM-58.

6. The catalyst system of claim 1, wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, and ZSM-20.

7. The catalyst system of claim 1, wherein said first molecular sieve comprises at least one of ZSM-5, ZSM-11, ZSM-22, ZSM-23, ZSM-35, ZSM-48, ZSM-57 and ZSM-58, and wherein said second molecular sieve comprises at least one of zeolite beta, zeolite Y, Ultrastable Y (USY), Dealuminized Y (Deal Y), mordenite, NU-87, ZSM-3, ZSM-4 (Mazzite), ZSM-12, ZSM-18, MCM-22, MCM-36, MCM-49, MCM-56, EMM-10, EMM-10-P, and ZSM-20.

8. The catalyst system of claim 1, wherein said third molecular sieve is selected from at least one of ZSM-5, ZSM-11, ZSM-12, zeolite beta, ZSM-22, ZSM-23, ZSM-35, ZSM-48, ZSM-57, and ZSM-58.

* * * * *